United States Patent [19]

Mullane et al.

[11] 4,324,246
[45] Apr. 13, 1982

[54] DISPOSABLE ABSORBENT ARTICLE HAVING A STAIN RESISTANT TOPSHEET

[75] Inventors: William I. Mullane, Wyoming, Ohio; Douglas J. Smith, Woodbury, Minn.

[73] Assignee: The Procter & Gamble Company, Cincinnati, Ohio

[21] Appl. No.: 148,657

[22] Filed: May 12, 1980

[51] Int. Cl.³ .............................................. A41B 13/02
[52] U.S. Cl. ............................ 128/287; 128/DIG. 30
[58] Field of Search ...................... 128/287, DIG. 30; 428/284, 286, 296

[56] References Cited

U.S. PATENT DOCUMENTS

| | | | |
|---|---|---|---|
| 3,560,601 | 2/1971 | Johnson | 128/287 |
| 3,814,101 | 6/1974 | Kozak | 128/287 |
| 3,815,602 | 6/1974 | Johns | 128/287 |
| 3,875,942 | 4/1975 | Roberts | 128/287 |
| 3,897,784 | 8/1975 | Fitzgerald | 128/287 |
| 3,929,135 | 12/1975 | Thompson | 128/287 |
| 3,967,623 | 7/1976 | Butterworth | 128/287 |
| 3,979,494 | 9/1976 | Ericson | 128/287 |
| 3,987,792 | 10/1976 | Hernandez | 128/287 |

*Primary Examiner*—Marion McCamish
*Attorney, Agent, or Firm*—John M. Pollaro; Fredrick H. Braun; Richard C. Witte

[57] ABSTRACT

An article of manufacture is disclosed for absorbing liquids, particularly body exudates such as menstrual discharges. An apertured formed film topsheet having a layer of fibers affixed to the inner surface thereof overlays an intermediate layer having a multiplicity of tapered capillaries. The apertured formed film topsheet has a specified combination of caliper, percent open area and percent of apertures having an equivalent hydraulic diameter less than or equal to 0.025 inches (0.064 cm.) which impart a stain resistant character to the topsheet.

8 Claims, 5 Drawing Figures

U.S. Patent  Apr. 13, 1982  4,324,246
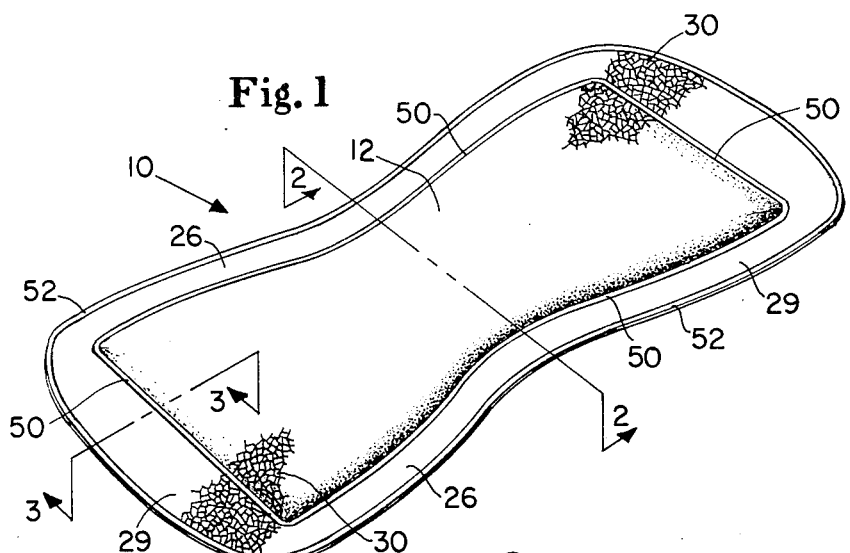
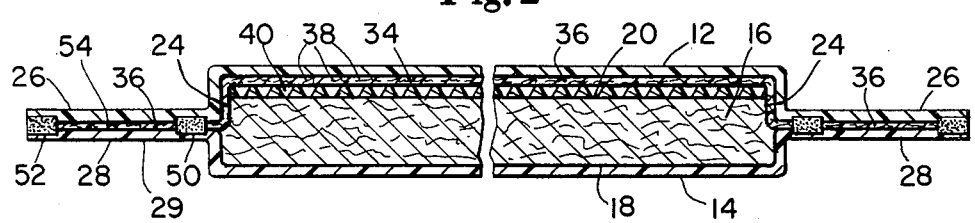
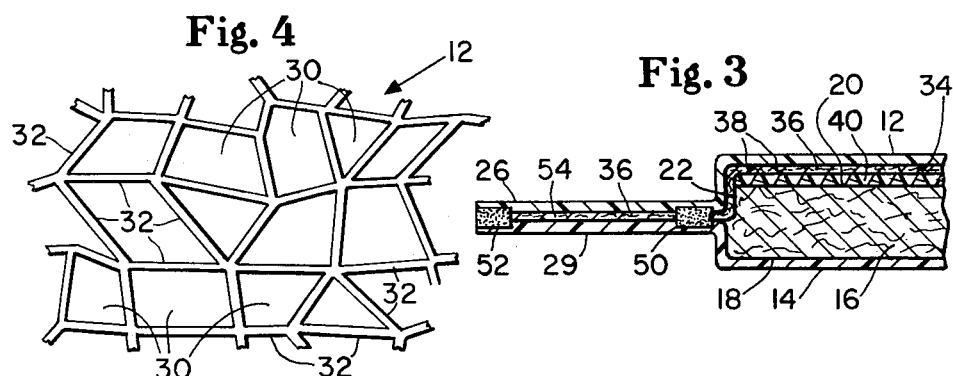
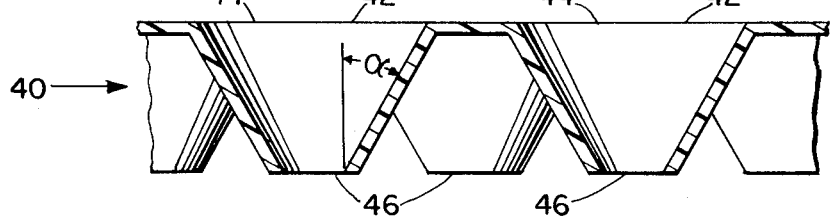

DISPOSABLE ABSORBENT ARTICLE HAVING A STAIN RESISTANT TOPSHEET

BACKGROUND OF THE INVENTION

This invention relates to disposable absorbent articles generally, and more particularly relates to catamenial pads and the like. Still more particularly, this invention relates to catamenial pads having an apertured formed film topsheet which has a layer of fibers adhered to the innersurface thereof. Further, this invention relates to catamenial pads having an embossed and apertured film interposed between a topsheet and an absorbent core and having a border which is provided with a channel disposed about the periphery of the catamenial pad.

Disposable absorbent articles are well known in the prior art and have many uses. For example, disposable diapers are intended to absorb and contain urine and feces; bandages are intended to absorb and contain blood and other body exudates while catamenial pads are intended to absorb and retain menstrual fluids and other vaginal discharges. In each instance the disposable absorbent article absorbs and retains a liquid, thereby preventing that liquid from soiling or otherwise contaminating the vicinity surrounding the area of liquid discharge.

In general, disposable absorbent articles all have the same basic structure: an absorbent core which is encased between a liquid permeable user contacting topsheet and a liquid impermeable backsheet. The prior art teaches numerous variations of and elements in addition to the basic topsheet, backsheet, and absorbent core arrangement, with each variation or additional element being directed to improving a specific characteristic of the disposable absorbent article.

Ideally, a disposable absorbent article will exhibit good strikethrough and rewet characteristics permitting liquid to rapidly penetrate the topsheet and preventing the liquid from flowing back through the topsheet. It is also an advantageous characteristic for the disposable absorbent article to present a clean user contacting surface, (i.e., the topsheet does not stain or retain liquid) and for the disposable absorbent article to protect the garments, clothing, bedding, etc. which surround the disposable article in use.

It is therefore an object of the present invention to provide a disposable absorbent article having improved rewet and strikethrough characteristics.

It is another object of the present invention to provide a disposable absorbent article having improved surface cleanliness and stain resistance.

It is a further object of the present invention to provide a disposable absorbent article providing improved protection against soiling of the vicinity surrounding the area of liquid discharge.

These and other objects of the invention will be readily apparent when considered in reference to the following description and when taken in connection with the accompanying drawings.

SUMMARY OF THE INVENTION

According to the present invention, a disposable absorbent article such as a catamenial pad is manufactured such that an absorbent core is encased between a liquid permeable topsheet and a liquid impermeable backsheet.

A preferred topsheet is manufactured from an apertured formed film having a caliper of less than about 0.030 inches (0.075 cm.), a percent open area of at least 35% and with less than 25% of the apertures having an equivalent hydraulic diameter smaller than or equal to 0.025 inches (0.064 cm.).

BRIEF DESCRIPTION OF THE DRAWINGS

FIG. 1 is a perspective view of a catamenial pad incorporating the present invention.

FIG. 2 is a section view taken along section 2—2 of FIG. 1.

FIG. 3 is a section view taken along section 3—3 of FIG. 1.

FIG. 4 is a greatly enlarged top view of the apertured formed film topsheet of the present invention.

FIG. 5 is a greatly enlarged edge view of the intermediate layer of the present invention.

DESCRIPTION OF A PREFERRED EMBODIMENT

Referring now to the drawings, there is shown a preferred embodiment of the present invention as it would be used in a disposable absorbent article and, in particular, in a catamenial pad. It should be understood, however, that the present invention is also applicable for use in other disposable absorbent articles such as diapers, bandages and the like. As used herein, the term "disposable absorbent article" refers to articles which are intended to absorb and contain liquids such as those discharged from the human body (e.g., blood, menses, urine), and further, which articles are intended to be discarded after a single use (i.e., they are not intended to be laundered or otherwise restored and then reused). A catamenial pad is a disposable absorbent article which is worn by females external to the urogenital region and which is intended to absorb and contain menstrual fluids and other vaginal discharges.

FIG. 1 is a perspective view of a catamenial pad 10 incorporating the present invention. As best seen in FIG. 2, however, the catamenial pad 10 basically comprises a liquid permeable topsheet 12, a liquid impermeable backsheet 14, and an absorbent core 16. The absorbent core 16 has first and second opposed faces, 18 and 20, respectively. The backsheet 14 overlays first opposed face 18 and is in contact with the user's undergarments when the catamenial pad 10 is worn. The topsheet 12 overlays second opposed face 20 and is placed against the user's body when the catamenial pad 10 is worn.

The topsheet 12 is preferably affixed to the backsheet 14. The backsheet 14 may be affixed to topsheet 12 in any manner and in any configuration as is well known in the catamenial pad art such as by using a hot melt adhesive such as marketed by Eastman Chemical Products Company of Kingsport, Tenn. under the tradename Eastobond A-3.

In a preferred manner and configuration of affixing the topsheet 12 to the backsheet 14, the topsheet 12 and the backsheet 14 are manufactured having a shape similar to but generally larger than the absorbent core 16. Thus, the topsheet 12 and the backsheet 14 have a topsheet flap 26 and a backsheet flap 28, respectively, extending outward from the lateral edges 22 and the longitudinal edges 24 of absorbent core 16. The topsheet flap 26 is affixed to the backsheet flap 28, thereby forming thin and flexible border 29 which encircles the absorbent core 16. Encircling the absorbent core 16 gives the border 29 a shape retaining character. Thus, in use the border 29 will not fold onto itself but rather will remain outwardly projecting from the lateral and longitudinal edges 22 and 24, respectively, of the absorbent core 16.

The border 29 provides improved protection against soiling of the vicinity surrounding the area of liquid discharge compared to the same disposable absorbent article not having the border 29. Accordingly, the border 29 has a width sufficient to prevent discharged liquid which is not absorbed by the absorbent core 16 from soiling the garments, clothing, bedding, etc. which are in close proximity to the point of liquid discharge. For example, in the catamenial pad 10 of a preferred embodiment, the border 29 has a width sufficient to assure that the catamenial pad 10 covers the crotch area of the wearer's undergarments. The border 29 preferably extends outward from the lateral edges 22 and longitudinal edges 24 of absorbent core 16 a distance of from about 0.125 inches (0.318 cm.) to about 1.0 inches (2.54 cm.) and most preferably from about 0.25 to about 0.75 inches (about 0.63 to about 1.9 cm.). The border 29 may have a uniform width or may have a width which varies about the periphery of catamenial pad 10.

While the border 29 has a shape retaining character in use, it is thin, flexible, comfortable, and readily conforms to the shape of the vicinity surrounding the point of liquid discharge such as the urogenital region of the body. The border 29 may be formed by affixing the topsheet flap 26 to the backsheet flap 28 across the entire width of the border 29 by gluing as hereinbefore described. A particularly preferred arrangement of the border 29, however, is shown in FIGS. 2 and 3.

As shown in FIGS. 2 and 3, the topsheet flap 26 is affixed to the backsheet flap 28 along both an inward seam 50 and an outward seam 52, forming a channel 54. The inward seam 50 is positioned adjacent to the absorbent core 16 and the outward seam 52 is spaced therefrom, preferably being positioned adjacent the edge of the border 29. The channel 54 is therefore bounded by the inward seam 50, the outward seam 52, the topsheet 12 and the backsheet 14. The topsheet 12 and the backsheet 14 are not affixed to each other between the inward seam 50 and the outward seam 52. The width of the channel 54 is at least 0.0625 inch (0.159 cm.) and preferably at least 0.5 inch (1.3 cm.).

The inward seam 50 and the outward seam 52 completely encircle the absorbent core 16 and are liquid impermeable, thereby inhibiting the lateral migration of liquid toward the edges of the catamenial pad 10.

Any of the well known techniques for affixing the topsheet 12 to the backsheet 14 may be used to form the inward seam 50 and the outward seam 52. For example, various well known heat bonding or gluing procedures may be used. In a most preferred embodiment, the topsheet flap 26 is ultrasonically bonded to the backsheet flap 28 along the inward seam 50 and outward seam 52 using the equipment and methods which are well known in the ultrasonic bonding art.

The backsheet 14 is impervious to liquid and prevents liquid absorbed by the absorbent core 16 from soiling the undergarments of the catamenial pad 10 wearer. Preferably, backsheet 14 is a polyethylene film of from about 0.0005 to about 0.002 inches (about 0.012 to about 0.051 mm.) thick although other flexible, liquid impervious materials may also be used. As used herein, the term "flexible" refers to materials which are compliant and which readily conform to the shape and contours of the human body.

Referring again to FIG. 2, it can be seen that absorbent core 16 is positioned between and encased by the topsheet 12 and the backsheet 14. Absorbent core 16 is generally compressible, conformable and non-irritating to the user's skin. The absorbent core 16 may be manufactured in a wide variety of sizes and from a wide variety of absorbent materials such as absorbent foams, which are commonly used in disposable absorbent articles and which are capable of absorbing and retaining liquids. Other materials can also be used for the absorbent core 16 such as a multiplicity of plies of creped cellulose wadding or any equivalent material. The absorbent capacity of the material used, however, must be sufficient to absorb and retain the expected liquid loading in the intended use of the absorbent article. In a preferred embodiment of a catamenial pad 10 intended to receive heavy menstrual discharges of approximately 40 ml., about 6 gms. of comminuted wood pulp generally referred to as airfelt was used with good results.

The shape and dimensions of the absorbent core 16 are selected to fit the urogenital region of wearer's of the catamenial pad 10. While the shape and dimensions may be varied, it has been found that a generally hourglass shaped absorbent core 16 having a length of about 7.5 inches (19.2 cm.), a maximum width of about 2.5 inches (6.4 cm.) and a minimum width at the midpoint of about 2.0 inches (5.1 cm.) provides good results. However, other dimensions and even other shapes (e.g. rectangular) may also be used for absorbent core 16.

The topsheet 12 is liquid permeable and contacts the skin of the catamenial pad 10 wearer. The topsheet 12 is compliant, soft feeling and non-irritating to the wearer's skin. Further, the topsheet 12 is preferably manufactured from hydrophobic materials using any of the well known processes for manufacturing a liquid permeable web. Accordingly, the topsheet 12 may, for example, be carded, spunbonded, melt blown or airlaid and may be fibrous or may be a continuous film which is either apertured or embossed and apertured.

A preferred topsheet 12 is an apertured hydrophobic film. FIG. 4 illustrates a particularly preferred topsheet 12 which is an apertured hydrophobic formed film. As used herein, the term "hydrophobic" refers to materials on which liquid will not spread and which have a contact angle greater than about 50°. The contact angle is the angle within the water drop between the water/air interface and the water/solid interface at the common junction of these two interfaces. The contact angle may be determined using any of the procedures as are well known such as those detailed in the book by A. Adamson entitled *Physical Chemistry of Surfaces* (2nd Ed. 1967) which book is incorporated herein by reference. Further, as used herein, the term "formed film" refers to topsheets 12 which are a continuous layer of polymeric material which has been provided with embossments.

The apertured formed film topsheet 12 which is preferred is manufactured in accordance with the procedures herein set forth and is provided with a multiplicity of apertures 30 (FIG. 4) which are separated by land portions 32. The ratio of the area of the apertures 30 to the total area of the topsheet 12 multiplied by 100 is the percent open area of the topsheet 12. The larger the percent open area, the more readily the topsheet 12 will permit liquid to enter the absorbent core. Too large a percent open area will, however, reduce the strength of the topsheet 12.

The preferred formed film topsheet 12 has a percent open area of at least 35 percent. Preferably, the formed film topsheet 12 has a percent open area of at least 45 percent and most preferably has a percent open area of at least 55 percent. The percent open area of the topsheet 12 represents the percent of the topsheet 12 which is open to the passage of liquids and indicates the permeability of the topsheet 12. Many procedures to determine the percent open area of the topsheet 12 will suggest themselves to one of ordinary skill. A procedure which was used with good results will now be described.

A 2 inch (5 cm.) square sample of the topsheet 12 is mounted in a standard 35 mm. photographic glass slide mount. The sample chosen should be representative of the porosity of the topsheet 12. If the porosity of the materials from which the topsheet 12 is manufactured cannot be represented by a single sample, the following procedure can be repeated for several samples and the results averaged.

The photographic slide holder containing the sample is inserted in a slide projector and projected onto a conventional viewing screen. While any conventional slide projector may be used, Ektagraphic Model AF2, fitted with an Ektamer 4-6 inch zoom lens (f:35) as manufactured by the Kodak Corporation of Rochester, N.Y. was used with satisfactory results. The projector is aimed at the center of the viewing screen and is placed at a distance of approximately 122 inches (310 cm.) perpendicularly from the viewing screen. The projector is vertically and horizontally centered on the viewing screen.

The projected image is photographed using any suitable camera. For example, a two second time exposure taken at an f stop of 8 with a Model F2 35 mm. camera as manufactured by the Nikon Corporation of Japan was used with good results. The camera had a micro-Nikkor P1:3.5 lens (f:55 mm.) and was used with Vericolor II 5025 type S film as manufactured by the Kodak Corporation. The camera was placed at a distance of approximately 115 inches (292 cm.) perpendicularly from the viewing screen. The camera is displaced along the vertical center line of the viewing screen a distance of approximately 3 inches (18 cm.) and is displaced along the horizontal center line of the viewing screen a distance of approximately 4 inches (10 cm.) from the center of the viewing screen.

In the photograph of the projected sample, the open area in the material will appear as light areas while the solid portions of the material will appear dark. The fraction of the topsheet 12 which is open area is determined by finding the fraction of light areas on the photograph.

The accuracy of the photographic procedure may be increased by enhancing the contrast between the light and dark areas of the photograph. The contrast enhancing procedure may be necessary, particularly for thin, transluscent perforated plastic films. The contrast between light and dark areas can be intensified, for example, by using a lens filter such as the green high contrast filter No. 563156 as manufactured by Schott Glasse Werks of Mainz, W. Ger. placed between the projector bulb and the sample.

From the photographs of each sample of topsheet 12, the percent open area can be determined using any appropriate method. It has been found that stochastic methods, such as a Monte Carlo technique works well. Accordingly, a series of random points or dots is generated and plotted on a transparent sheet which covers at least 12 square inches (77 square cm.) of the photograph being analyzed. A suitable sheet having random dots already plotted is the Bruning Areagraph Chart 4849 manufactured by Bruning Division of Addressograph Multigraph Corporation of Cleveland, Ohio.

The transparent sheet is laid over the photograph of the topsheet 12 and the light points (i.e., the number of random dots having at least half of their total area covering a light area) are counted. The ratio of light points to the total number of dots within the area of the photograph when expressed as a percentage is the percent open area of the topsheet 12 being analyzed.

The foregoing procedure may be simplified by enlarging the photographs. For example, the negatives for apertured formed film samples were enlarged to 8 inch by 10 inch (20 cm.×25 cm.) photographs while the negatives for nonwoven samples were enlarged to 16 inch by 20 inch (41 cm.×51 cm.) photographs. It should be noted that nonwoven samples have fibers lying in more than one plane which makes the foregoing procedure difficult to use.

Methods of determining the percent open area other than as specifically described will suggest themselves to one skilled in the art. These other methods may be used so long as they give a true representation of the percentage of open area of the topsheet 12.

The caliper of the preferred apertured formed film topsheet 12 is also important. If the caliper of the topsheet 12 is too great, liquid will accumulate in the apertures 30 and not pass into the absorbent core 16. The topsheet 12 will then have a stained appearance.

The preferred apertured formed film topsheet 12 also has a caliper of less than about 0.030 inches (0.075 cm.) and preferably less than about 0.025 inches (0.064 cm.). The caliper of the topsheet 12 may be determined using any standard technique. For example, an Ames Micrometer as manufactured by the Ames Corporation of Waltham, Mass. was used and found to be satisfactory.

The apertures 30 are preferably irregularly shaped openings randomly distributed in the topsheet 12. The apertures 30 may be of equal or of different sizes provided that less than about 25 percent of the apertures 30 have a small equivalent hydraulic diameter (EHD). Apertures 30 having a small EHD will attract and hold liquid due to the high capillary attraction of these apertures. If the percentage of the apertures 30 in the topsheet 12 is not less than 25 percent, the topsheet 12 will appear stained. Accordingly, less than 25% of the apertures 30 have an EHD less than or equal to about 0.025 inches (0.064 cm.). As used herein, the term equivalent hydraulic diameter is defined by the following equation:

$$EHD = 4 \times A/P$$

where:
EHD is the equivalent hydraulic diameter
A is the area of the aperture 30
P is the perimeter of the aperture 30
The equivalent hydraulic diameter is the diameter of a circular aperture having fluid flow characteristics similar to the irregular aperture for which the calculation is being done.

The percent of the apertures 30 having an equivalent hydraulic diameter (EHD) less than a specified value may be determined by calculating the EHD for each aperture 30 in a representative sample of the topsheet 12. The number of apertures having an EHD less than the specified value divided by the total number of apertures 30 and multiplied by 100 is the percent of apertures having an EHD less than the specified value. The EHD of each aperture 30 may be easily calculated from photographs taken in accordance with the procedure hereinbefore described provided care is taken to properly consider the magnification factor used. It has been found that placing a scale over the sample being photographed and enlarging the scale with the photograph works well to provide a reference for determining the EHD.

Nonwoven materials differ from film materials and are characterized by a large number of fibers which overlap each other. In particular, the fibers of a nonwoven material overlaps each other throughout the thickness of the material (i.e., the fibers lay atop each other), thereby forming tortuous liquid flow paths. Accordingly, more than 25% of the apertures in nonwoven materials will inherently have EHD's less than the hereinbefore specified values [i.e., less than or equal to 0.025 inches (0.064 cm.)].

The apertured formed film topsheet 12 may be manufactured using any of the well known processes for producing formed films. A preferred topsheet 12 was made according to the following procedure.

A sample of thermoplastic material such as an 0.0015 inch (0.0038 cm.) thick polyethylene film is heated above its softening point. The softening point is the temperature at which the thermoplastic material can be formed or molded and is less than the melting point of the material. The heated thermoplastic material is brought into contact with a heated forming screen. The forming screen is preferably an apertured wire mesh screen having the desired aperture size, pattern and configuration. A vacuum is used to draw the heated film against the forming screen, thereby forming the film into the desired pattern. While the vacuum is still being applied to the film, a jet of hot air is passed over the film. The hot air jet perforates the film in a pattern corresponding to the pattern of apertures in the forming screen.

When an apertured formed film having the specified caliper, percent open area, and percent of apertures having a small EHD is used for topsheet 12, the catamenial pad 10 exhibits improved surface cleanliness and stain resistance in use. Cleanliness and stain resistance can be determined using the following procedure.

A synthetic menstrual fluid is prepared by adding approximately 15 grams of the pulp from oranges to 100 milliliters of a 9 percent sodium chloride solution and blending for about 1 minute. Four grams of crystalline bovine albumin are dissolved in the sodium chloride solution and 33 milliliters of whole blood together with 25 grams of egg white are added. The mixture is stirred until it is uniform. While any synthetic menstrual fluid can be used, it is important that the fibrous and mucosal components of menses be simulated.

A grading scale for determining the cleanliness rating of various topsheets 12 is prepared. A substrate which will retain all of the synthetic menstrual fluid placed on it is selected and several substrate samples prepare. A spun bonded polyester nonwoven web having a basis weight of 0.5 ounces per square yard (17 g/m²) as manufactured by E. I. DuPont deNemours of Wilmington, Del. and marketed under the tradename T-310 was used with good results. Varying amounts of the synthetic menstrual fluid are applied to a 1 inch by 3 inch (2.5×7.6 cm.) rectangular portion of each substrate sample. For the grading scale used to generate the data in Table I, 8 substrate samples were treated with 0, 0.1, 0.25, 0.50, 1.0, 1.5, 2.0, and 4.0 milliliters of synthetic menstrual fluid. No absorbent core was provided beneath the substrate sample. Therefore, all of the menstrual fluid placed on the substrate sample remained on the substrate sample. The menstrual fluid was allowed to dry and each substrate sample was assigned a value ranging from 0 to 7 respectively. Thus, the sample treated with no synthetic menstrual fluid was assigned a value of zero and indicates a clean substrate while the sample treated with 4.0 ml. of synthetic menstrual fluid was assigned a value of 7 and indicates a heavily soiled substrate.

The topsheet 12 to be tested is placed over an absorbent core and 4.0 ml. of synthetic menstrual fluid spread over a 1 inch by 3 inch (2.5×7.6 cm.) rectangle of the topsheet 12. After 60 seconds, the topsheet 12 material is removed from the absorbent core and allowed to dry. To facilitate the even distribution of the synthetic menstrual fluid over the 1 inch by 3 inch (2.5×7.6 cm.) rectangle, a small amount of synthetic menstrual fluid (0.2-0.3 ml.) can be spread over the rectangle before the topsheet 12 material is placed over the absorbent core.

The stained topsheet 12 material is compared to the grading scale to determine the cleanliness rating of the topsheet 12 being tested. The stained topsheet 12 is assigned a cleanliness rating determined by interpolation from the substrate samples used to establish the grading scale.

Lower cleanliness ratings indicate a topsheet 12 having a clean surface appearance and good stain resistance characteristics. As the cleanliness rating increases, so does the appearance of surface soiling.

It is clear from Table I that the cleanliness rating of sample 1 is superior to the other samples tested.

As seen in Table I, only sample 1 has the required caliper, percent open area, and percent of apertures having a small EHD as set forth hereinbefore. Samples 3 and 6 are nonwoven materials and, therefore, inherently have too high a percentage of apertures with small EHD's. Samples 2 and 5 are apertured formed films, as is sample 1, but sample 2 does not have the required percent open area and sample 5 does not have the required caliper. Finally, sample 4 is an apertured film (i.e., it is not formed) but with a percentage of apertures having a small EHD above the required limit. Only in sample 1 where the caliper, percent open area, and percent of apertures having a small EHD are within the limits hereinbefore set forth does the topsheet 12 exhibit a clean surface appearance and good stain resistance characteristics.

TABLE I

Cleanliness Ratings for Topsheet Samples Having Various Characteristics

| Topsheet Sample | Cleanliness Rating | Caliper (in.) | % of Apertures Having an Equivalent Hydraulic Diameter less than or equal to 0.025 inches | % Open Area |
|---|---|---|---|---|
| 1[1] | 1.8 | 0.021 | 21 | 42 |
| 2[1] | 3.6 | 0.025 | 0 | 28 |
| 3[2] | 3.7 | 0.006 | 100 | 28 |
| 4[3] | 4.5 | 0.002 | 100 | 57 |
| 5[1] | 5.1 | 0.035 | 0 | 55 |
| 6[2] | 5.2 | 0.013 | 100 | 37 |

Notes:
[1] Samples 1, 2 and 5 are apertured formed films.
[2] Samples 3 and 6 are nonwoven.
[3] Sample 4 is an apertured film.

Referring again to FIGS. 2 and 3, it can be seen that a preferred embodiment of the catamenial pad 10 is provided with a thin layer 36 comprising a multiplicity of individual fibers 38 which are evenly dispersed over and affixed to the inner surface 34 of the topsheet 12. The inner surface 34 is that surface of the topsheet 12 which faces toward the absorbent core 16. The fibers 38 may be of any suitable material and are preferably less hydrophobic than the topsheet 12. For example, fibers of polyester, nylon, rayon, and cotton have been used with good results. A preferred fiber 38 is derived from wood by a thermomechanical pulping process as is well known. Wood fibers derived from other pulping processes such as a chemical pulping process may also be used.

The length and width of the fibers 38 may be varied. Thus, fibers 38 having a width of from about 15 to about 40 microns and a length of from about 1.0 to about 3.5 mm. have been found to be satisfactory. While the weight of the layer 36 may also be varied, it has been found that at least about 1.5 grams of the fibers 38 per square meter of the topsheet 12 and preferably at least about 3.1 grams of the fibers 38 per square meter of the topsheet 12 must be evenly distributed on and affixed to the inner surface 34.

The inner surface 34 of the topsheet 12 may be provided with a layer 36 of fibers 38 using the following procedure. An adhesive suitable for affixing the fibers 38 to the topsheet 12 is applied to the inner surface 34. An acrylic binder as manufactured by Rohm & Haas of Philadelphia, Pa. and marketed under the tradename Rhoplex HA-8 was sprayed on the inner surface 34 with good results. The quantity of adhesive used may be varied, but from about 6 to about 12 grams of adhesive per square meter of topsheet 12 was found to be suitable when the Rhoplex HA-8 adhesive was used.

Before the adhesive sets, the fibers 38 are flocked onto inner surface 34. The flocking operation is conveniently done by placing the fibers 38 in a sieve and shaking the sieve over the topsheet 12 until the desired quantity of fibers 38 have been deposited on the inner surface 34. A sieve having openings of about 0.066 inches (0.17 cm.) such as a number 12 Tyler mesh sieve as manufactured by the W. S. Tyler Company of Cleveland, Ohio gave satisfactory results.

The topsheets 12 which are provided with a layer 36 of fibers 38 exhibit improved strikethrough characteristics. Strikethrough is a measure of the time taken for liquid to penetrate through the topsheet 12. Rapid liquid penetration of the topsheet 12 (i.e., a low strikethrough time) is important to reduce the possibility of liquid running across the surface of the topsheet 12 and leaking past the sides of the catamenial pad 10 before being absorbed by the absorbent core 16.

The strikethrough time of a topsheet 12 may be determined using any suitable procedure which will measure the time it takes for liquid to penetrate the topsheet 12. The following procedure has been used with good results.

A 4 inch by 4 inch (10 cm. × 10 cm.) sample of topsheet 12 is placed over an absorbent core which has preferably been conditioned or stored at 73° F. (24° C.) and 50% relative humidity to help eliminate variations in the data due to varying moisture contents of the absorbent cores. The absorbent core of each test sample is comminuted wood pulp weighing from 2.4 to 3.0 grams with a density of from 0.7 to 0.85 gm/cu.cm. A 4 inch × 4 inch (10 cm. × 10 cm.) plate weighing 800 grams and having an 0.25 inch (6.3 mm.) diameter hole centered therein is placed on the topsheet 12. The hole traverses the thickness of the plate and is filled with 5 ml of a liquid having a surface tension of about 47 dynes. The time required for the 5 ml of liquid to penetrate the topsheet 12 is the strikethrough time. The shorter the strikethrough time the better the strikethrough characteristic of the topsheet 12.

Several samples of an apertured formed film topsheet 12 having a percent open area of about 42 percent, a caliper of about 0.021 inches (0.053 cm.) and with about 21 percent of the apertures 30 having an equivalent hydraulic diameter less than or equal to 0.025 inches (0.064 cm.) were provided with a layer 36 of fibers 38 using the foregoing procedure. The quantity of fibers 38 applied to each sample was varied, but for each sample the fibers 38 were wood fibers derived by a thermomechanical pulping process. The strikethrough times for each of the samples thus prepared was determined and are presented in Table II. The foregoing procedure was used to determine the data presented in Table II except that the 800 gram plate was not used. Instead, the 5 ml. of liquid were dropped directed onto the sample being tested to simulate the in-use condition when the disposable absorbent article is not under load. As can be seen from Table II, a significant improvement in strikethrough is obtained by providing topsheet 12 with a layer 36 of fibers 38 that has at least 1.5 grams of fibers 38 per square meter of topsheet 12.

TABLE II

Relationship Between Fiber Quantity And Strikethrough Time

| Sample[1] | Fiber Quantity gms. of fiber/ sq. m of topsheet[2] | Strikethrough Time (sec.)[3] |
|---|---|---|
| 1 | 0 | 26.0 |
| 2 | 0.5 | 12.3 |
| 3 | 1.5 | 6.4 |
| 4 | 3.1 | 3.8 |
| 5 | 4.6 | 4.1 |
| 6 | 9.3 | 2.2 |

Notes:
[1] All samples utilized an apertured formed film topsheet having a percent open area of about 42 percent, a caliper of about 0.021 inches (0.053 cm.) and with about 21 percent of the apertures 30 having an EHD less than or equal to 0.025 inches (0.064 cm.).
[2] The fibers used were wood fibers derived from a thermomechanical pulping process.
[3] Strikethrough times were determined using the procedure hereinbefore set forth that the 800 gram plate was not used.

TABLE III

| Topsheet Sample (Material/ manufacturing method) | Strikethrough Time (Sec.) | |
|---|---|---|
| | Without a Layer of Fibers | With a Layer of Fibers[1] |
| Rayon/airlaid nonwoven[2] | 107 | 4.0 |
| Polyester/spunbonded nonwoven[3] | 50 | 2.4 |
| Polypropylene/airlaid nonwoven[4] | 120 | 8.5 |

Notes:
[1] The layer of fibers used for all samples was about 3.7 grams of the fibers 38 per square meter of the topsheet 12. The fibers 38 were wood fibers derived by a thermomechanical pulping process and adhered to the inner surface 34 using an acrylic binder.
[2] As manufactured by The Kendall Company, Fiber Products Division of Boston, Massachusetts and marketed under the tradename Maralay.
[3] As manufactured by E. I. DuPont de NeMours & Company, Inc. of Wilmington, Delaware and marketed under the tradename Remay.
[4] As manufactured by the Kendall Company, Fiber Products Division of Boston, Massachusetts and marketed under the tradename Webril.

While the data presented in Table II was determined for a sample of an apertured form film topsheet 12 similar improvements in the strikethrough characteristics of the topsheet 12 can be obtained for topsheets 12 manufactured from other processes (e.g., nonwoven process) or from other materials (e.g., rayon). Samples of the topsheets 12 other than apertured formed films were provided with a layer 36 of fibers 38 and tested to determine their respective strikethrough times using the foregoing procedures and methods. The results of the strikethrough tests on these samples is presented in Table III.

As can be seen from Table III, a significant improvement is obtained by providing the topsheet 12 with a layer 36 of fibers irrespective of the material or manufacturing method used for the topsheet 12.

Referring again to FIGS. 2 and 3, it can be seen that a preferred catamenial pad 10 has an intermediate layer 40 interposed between the topsheet 12 and the absorbent core 16. More specifically, in the embodiment illustrated in FIGS. 2 and 3, the intermediate layer 40 is interposed between the apertured formed film topsheet 12 which has a layer 36 of fibers 38 affixed to the undersurface 34 and the absorbent core 16. Preferably, intermediate layer 40 is coterminus with the second opposed face 20 of the absorbent core 16 and is affixed to the topsheet 12 in any suitable manner such as by gluing. A suitable adhesive is manufactured by the Eastman Chemical Products Company of Kingsport, Tenn. and marketed under the tradename Eastobond A-3.

FIG. 5 is an edge view of the intermediate layer 40. As seen in FIG. 5, intermediate layer 40 has a plurality of tapered capillaries 42, each of which has a base opening 44 and an apex opening 46.

Apex openings 46 are in intimate contact with absorbent core 16 and base openings 44 contact the layer 36 of fibers 38. Further, base openings 44 and apex openings 46 are spaced apart from each other so as to form tapered capillaries 42.

Intermediate layer 40 is manufactured from a liquid impervious material such as low density polyethylene film having a thickness of from about 0.001 to about 0.002 inches (0.0025 to 0.0051 cm.). The liquid impervious material is provided with a multiplicity of tapered capillaries 42 in a manner, size, configuration, and orientation as generally set forth in U.S. Pat. No. 3,929,135 entitled Absorptive Struture having Tapered Capillaries which issued to Hugh A. Thompson on Dec. 30, 1975, which patent is incorporated herein by reference. Accordingly, tapered capillaries 42 have an angle of taper (FIG. 5) of from about 10° to about 60°, a base opening dimension of from about 0.006 to about 0.250 inches (preferably from about 0.030 to about 0.060 inches) and an apex opening of from about 0.004 inches to about 0.100 inches (preferably from about 0.005 to about 0.050 inches).

The catamenial pad 10 having the intermediate layer 40 interposed between the formed film topsheet 12 having a layer 36 of fibers 38 affixed to the inner surface 34 and the absorbent core 16 exhibits improved rewet characteristics. The rewet value is a measure of the amount of liquid which flows from the absorbent core 16 to the outer surface of the topsheet 12. Large quantities of liquid on the outer surface of the topsheet 12 (i.e. high rewet values) are undesirable because they lead to the discomfort of the wearer of the disposable absorbent article.

The rewet value of a disposable absorbent article may be determined using any suitable procedure. A procedure which was used with good results will now be described.

A 4 inch by 4 inch (10×10 cm.) test sample is prepared and is preferably conditioned or stored at 73° F. (24° C.) and 50% relative humidity to help eliminate variations in data due to varying moisture contents of the samples. The absorbent core of each test sample is comminuted wood pulp weighing from 2.4 to 3.0 grams with a density of from 0.7 to 0.85 gms/cu.cm. A quantity of liquid is discharged onto the topsheet of the test samples and allowed to penetrate into the absorbent core. Approximately 30 ml. of a liquid having a surface tension of about 47 dynes was discharged onto the topsheet of the sample and found to be a satisfactory quantity. To assure even distribution of the liquid within the absorbent core, the test sample is subjected to a pressure of about 0.25 psi (1.7 kilopascals) for about 3 minutes. The required pressure may be generated simply by placing a weight on the test sample. The weight is removed and two pieces of preweighed absorbent paper such as Whatman No. 4 filter paper are placed on the topsheet of the test sample. The weight is dried to remove any liquid from it and placed on the absorbent papers which have been placed on the test sample. After about 2 minutes, the absorbent papers are removed and reweighed to determine the quantity of liquid they have absorbed. The quantity of liquid absorbed by the absorbent papers is the rewet value of the sample tested.

Several test samples having an apertured formed film topsheet with an open area of about 42 percent, a caliper of about 0.021 inches (0.053 cm.) and with about 21 percent of the apertures 30 having an equivalent hydraulic diameter less than or equal to 0.025 inches (0.064 cm.) were tested to determine their rewet values and strikethrough times. The results of these tests are presented in Table IV.

As can be seen from Table IV, the combination of an apertured formed film topsheet 12 having a layer 36 of fibers 38 adhered to the inner surface 34 with the intermediate layer 40 (sample 4) has an improved rewet value without sacrificing strikethrough time. The combination of an apertured formed film topsheet 12 which does not have a layer 36 of fibers 38 and the intermediate layer 40 (sample 3) has favorable rewet values but an unacceptable high strikethrough time. Samples 1 and 2 did not have the intermediate layer 40, and they exhibit high rewet values.

TABLE IV

Rewet Values and Strikethrough Times for Samples Having Various Constructions

| Sample | Construction of Sample[1] | Strikethrough Time (sec.)[4] | Rewet Value (ml.) |
|---|---|---|---|
| 1 | Topsheet[2] | 1.0 | 0.5 |
| 2 | Topsheet with a layer of fibers[3] | 0.8 | 0.65 |
| 3 | Topsheet and an intermediate layer | 31.4 | 0.12 |
| 4 | Topsheet with a layer of fibers and an inter- | 1.5 | 0.11 |

TABLE IV-continued

Rewet Values and Strikethrough Times for
Samples Having Various Constructions

| Sample | Construction of Sample[1] | Strikethrough Time (sec.)[4] | Rewet Value (ml.) |
|---|---|---|---|
| | mediate layer[3] | | |

Notes:
[1] All samples also had an absorbent core as hereinbefore set forth.
[2] The topsheet for all samples was an apertured formed film having the percent open area, caliper, and percent of apertures having an equivalent hydraulic diameter less than or equal to 0.025 inches (0.064 cm.) as hereinbefore set forth.
[3] The layer of fibers was wood fibers derived by a thermomechanical pulping process and comprised about 3.7 grams of the fibers 38 per square meter of the topsheet 12. The fibers 38 were adhered to the inner surface 34 using an acrylic binder.
[4] Strikethrough times were determined in accordance with the procedure hereinbefore set forth utilizing the 800 gram plate.

In use, the catamenial pad 10 is positioned over the urogenital region of the wearer with the topsheet 12 contacting the wearer's body. The catamenial pad 10 may be held in place using any well known method such as by the use of belts worn about the waist of the user or by pinning to the wearer's garments. A preferred method of holding the catamenial pad 10 in place is to provide a band of adhesive on the backsheet 14 which affixes the catamenial pad 10 to the wearer's undergarments in an easily removable manner.

The catamenial pad 10 is comfortable, flexible, and readily conforms to the urogenital region of the wearer. Additionally, the border 29 is then and extends outward from the absorbent core 16 to completely overlay the crotch portion of the wearer's undergarments.

With the catamenial pad 10 in place, menstrual fluid and other vaginal excretions are discharged onto the topsheet 12. The apertured formed film topsheet 12 permits the discharged fluid to penetrate through to the absorbent core 16 while maintaining a clean stain resistant surface against the wearer. The layer 36 of fibers 38 affixed to the inner surface 34 of the topsheet 12 reduces the strikethrough time of the topsheet 12, thereby improving the ability of the discharged fluid to enter the absorbent core 16. The discharged fluid also passes through the intermediate layer 40 rapidly and is prevented from flowing back toward the topsheet 12 by the intermediate layer 40. Accordingly, the topsheet 12 does not present an excessively wet surface against the wearer.

Discharged fluids which flow across the topsheet 12 and beyond the absorbent core 16 will encounter the border 29. Discharged fluids which are absorbed by the absorbent core 16 are prevented from reaching the border 29 by the liquid impermeable inward seam 50. The border 29 therefore provides added protection against undergarment soiling without the increased bulkiness associated with the absorbent core 16. Further, discharged fluid encountering the border 29 will enter and be retained in the channel 54 where it is prevented from flowing outward to the edge of the catamenial pad 10 by the outward seam 52.

It will be understood by those skilled in the art that the invention has been described with reference to an exemplary embodiment and that variations and modifications can be effected in the described embodiment without departing from the scope and spirit of the invention.

For example, the border 29 provides added protection against soiling of the wearer's undergarments irrespective of whether or not topsheet 12 is provided with a layer 36 of fibers 38 and even irrespective of whether the topsheet 12 is an apertured formed film, a nonwoven web or any other liquid pervious material. Further, layer 36 of fibers 38 may be used to improve the strikethrough times of topsheets 12 which are other than apertured formed films. Thus, topsheet 12 which is carded, spun bonded, airlaid, apertured films or nonwovens, or of any other construction or of any material may be provided with a layer 36 of fibers 38 which are affixed to inner surface 34. Still further, intermediate layer 40 may be positioned over only a portion of absorbent core 16 or may be omitted entirely.

In order to more fully appreciate the spirit and scope of the invention, reference should be made to the appended claims.

What is claimed and desired to be secured by Letters Patent of the United States is:

1. A disposable absorbent article comprising:
    an absorbent core means for absorbing liquid, said absorbent core means having a first and a second opposed face;
    a liquid impermeable backsheet overlaying said first opposed face of said absorbent core means; and
    a liquid permeable topsheet overlaying said second opposed face of said absorbent core means, said topsheet being a hydrophobic film having a caliper of less than about 0.030 inches, said topsheet a multiplicity of apertures with less than about 25 percent of said apertures having an equivalent hydraulic diameter less than or equal to about 0.025 inches, said topsheet having a percent open area of at least about 35 percent.

2. The disposable absorbent article of claim 1 wherein said topsheet has a percent open area of at least about 45 percent.

3. The disposable absorbent article of claim 1 wherein said topsheet has a percent open area of at least about 55 percent.

4. The disposable absorbent article of claim 2 or 3 wherein said topsheet has a caliper less than about 0.025 inches.

5. A catamenial pad comprising:
    an absorbent core means for absorbing liquid, said absorbent core means having a first and a second opposed face;
    a liquid impermeable backsheet overlaying said first opposed face of said absorbent core means; and
    a liquid permeable topsheet overlaying said second opposed face of said absorbent core means, said topsheet being a hydrophobic film having a caliper of less than about 0.030 inches, said topsheet having a multiplicity of apertures with less than about 25 percent of said apertures having an equivalent hydraulic diameter less than or equal to about 0.025 inches, said topsheet having a percent open area of at least about 35 percent.

6. The catamenial pad of claim 5 wherein said topsheet has a percent open area of at least about 45 percent.

7. The catamenial pad of claim 5 wherein said topsheet has a percent open area of at least about 55 percent.

8. The catamenial pad of claim 6 or 7 wherein said topsheet has a caliper less than about 0.025 inches.

* * * * *